United States Patent [19]

Reznikoff et al.

[11] Patent Number: 4,980,290
[45] Date of Patent: Dec. 25, 1990

[54] HUMAN UROEPITHELIAL CELL

[75] Inventors: Catherine A. Reznikoff; Brian J. Christian, both of Madison, Wis.

[73] Assignee: Wisconsin Alumni Research Foundation, Madison, Wis.

[21] Appl. No.: 106,310

[22] Filed: Oct. 9, 1987

[51] Int. Cl.$^5$ .............................................. C12N 5/00
[52] U.S. Cl. .............................. 435/240.2; 435/240.23
[58] Field of Search ...................... 435/240.2, 1, 240.1, 435/240.23

[56] References Cited

PUBLICATIONS

C. Harris, 47 Cancer Res. 1–10 (1987).
J. Di Paolo, 70 JNCI 3–8 (1983).
A. Girardi et al., 65 J. Cell. Comp. Physiol. 69–83 (1965).
G. Sack, 17 In Vitro 1–19 (1981).
P. Kahn et al., 126 Virol. 348–360 (1983).
V. Defendi et al., 2 J. Cell. Phys. Supp. 131–140 (1982).
J. Rhim et al., 227 Science 1250–1252 (1985).
J. Rhim et al., 232 Science 385–388 (Apr. 1986).
B. Christian et al., 27 Proc. AACR 133 (May 1986).
S. Chang et al., 42 Cancer Res. 2040–2053 (1982).
M. Steinberg et al., 76 P. N. A. S. 801–805 (1979).
W. Schmidt et al., 132 J. Urol. 1262–1264 (1984).
C. Reznikoff, 19 in Vitro 326–343 (1983).
R. Ehrman et al., 16 J. Natl. Can. Inst. 1375–1390 (1956).
C. Reznikoff et al., 141 Proc. Soc. Exp. Biol. Med. 740–746 (1972).
T. Oberley et al., 4 Diagnostic Histopath. 117–128 (1981).
A. Hamburger et al., 197 Science 461–463 (1977).
Christian et al., *Proc. AACR 27* (133)1986. "Chemical Transformation of Human Urepithelial Cells Immortalized by SV40 Virus".
Rhim et al. *Science*, 232 1986. "Neoplastic Conversion of Humankeratinocytes by Adenovirus 12-SV40 Virus & Chemical Carcinogens".
Copenhaver et al. *Bailey's Textbook of Histology* 17th ed. Williams & Wilkins Co. Baltimore 1978 p. 108.
Freifelder, *Molecular Biology*, Jones & Barlett Publishers, Inc. 1983, p. 903.

*Primary Examiner*—Charles F. Warren
*Assistant Examiner*—George C. Elliott

[57] ABSTRACT

Immortalized human uroepithelial cells are disclosed. One cell line is not spontaneously tumorigenic, but can be tumorigenically transformed by certain carcinogens. Another is a tumorigenic variant that provides a source of epithelial keratins.

2 Claims, No Drawings

HUMAN UROEPITHELIAL CELL

This invention was made with U.S. Government support awarded by the National Institutes of Health (NIH), Grant No. #NCI CA 29525. The U.S. Government has certain rights in this invention.

The present invention relates to human uroepithelial (urinary tract) cell lines. More particularly it relates to immortalized human uroepithelial cells which are either keratin producing and tumorigenically transformable, or keratin producing and tumorigenic.

Background of the Invention

Bladder cancer is the third most prevalent cancer type among men sixty years of age and older. Further, the development and progression of bladder cancer may well illustrate principles applicable to other human cancers. There is therefore a need to develop appropriate experimental systems using cultured human uroepithelial cells. Such cells may provide useful sources of human proteins of interest (e.g. for antibody development), and provide useful in vitro test systems to help in the determination of whether a compound is carcinogenic. It is estimated that 80-90% of human cancers derive from epithelial cells. Thus, this cell type may have particular benefits for in vitro tests.

To date neoplastic transformation of cultured human epithelial cell types in vitro has been rarely and only inconsistently achieved. See C. Harris, 47 Cancer Res. 1-10 (1987) (article itself is not prior art); J. Di Paolo, 70 JNCI 3-8 (1983). The disclosure of these articles and all other articles recited herein are incorporated by reference as if fully set forth herein.

The stumbling blocks in the development of such in vitro transformation systems with human epithelial cells have been (1) the difficulty in growing cells in culture and (2) the difficulty in neoplastically transforming cultured cells using a single oncogenic agent. Recent advances in tissue culture technology have resolved to a great extent the first problem. An approach which has been used successfully to get around the latter problem is to use a two-step strategy to neoplastically transform cells. For example, certain viruses (SV40 or SV40-adeno hybrid) can be used to immortalize human epithelial cells (the first step). Such established cells can then sometimes be neoplastically transformed by treatment with a second carcinogenic agent (such as a test chemical).

The problem with the above approach is that cell lines immortalized by viruses typically have characteristics (e.g. production of infectious virus, loss or gain of chromosomes, or spontaneous transformation to tumorigenicity after time in culture) that greatly diminish their usefulness. For example, if chromosomes are grossly altered after the first step, it is difficult to determine if specific chromosomal alterations are important in the critical step leading to tumorigenicity. See generally A. Girardi et al., 65 J. Cell Comp. Physiol. 69-83 (1965); G. Sack, 17 In Vitro 1-19 (1981); P. Kahn et al., 126 Virol. 348-360 (1983); V. Defendi et al., 2 J. Cell Phys. Supp. 131-140 (1982); J. Rhim et al., 227 Science 1250-52 (1985); J. Rhim et al., 232 Science 385-388 (April 1986); S. Chang et al., 42 Cancer Res. 2040-2053 (1982). M. Sternberg et al., 76 P.N.A.S. 801-805 (1979). See also B. Christian, et al., 27 Proc. of ACCR 133 (May 1986).

Therefore, it is most desirable to provide an immortalized line of human and epithelial origin which is nontumorigenic, non-virus producing, tumorigenically transformable, and which has not lost or gained chromosomes.

SUMMARY OF THE INVENTION

As used herein, "balanced chromosome type" is intended to mean that the cells have no apparent loss or gain of chromosomes (and appear to substantially contain the genetic material of normal cells), as determined by karyotypic stain analysis, although in some cases the chromosomes may be rearranged and/or the whole set may be duplicated.

In one aspect of the invention there is provided a human uroepithelial cell that is established in culture, and that is of the balance chromosome type. It produces epithelial keratin, is SV40 transformed, and is not spontaneously tumorigenically transformed. The cell is capable of being preserved cryogenically and being tumorgenically transformed. Preferably, it will not spontaneously produce infectious SV40 virus.

In another aspect of the invention there is provided a human uroepithelial cell that is tumorigenic in an athymic nude mouse, is SV40 transformed, and is established in culture. The cell is also capable of being preserved cryogenically and producing uroepithelial keratin.

It is therefore an object of the invention to produce cell lines with the above characteristics. Still other objects and advantages of the present invention will be apparent from the description which follows.

DESCRIPTION OF THE PREFERRED EMBODIMENTS

A better understanding of the present invention will be accomplished by reference to the preferred embodiments. It should be understood, however, that the description of the preferred embodiments ar intended only as examples of the invention. They are not intended to represent the full scope of the invention. Rather, the claims should be looked to in order to determine the full scope of the invention.

A. Normal Cell Line—HUC

Cultures of normal human uroepithelial cells (HUC) can be obtained by procedures analogous to those described in W. Schmidt et al., 132 J. Urol. 1262-1264 (1984) and C. Reznikoff, 19 In Vitro 326-343 (1983). The ureter used to initiate the cultures SV-HUC-1 was derived from an 11-year-old male accident victim whose kidneys were donated for transplantation. The mucosal layer of tissue from a segment of the individual's ureter was separated from the underlying tissue with forceps, minced into approximately 1 mm$^2$ explants and plated ($\sim$30 explants/100 mm dish) onto type I rattail collagen-gel-coated dishes in approximately 1 ml of culture media. Ammonia-reconstituted collagen gels were prepared according to the method of R. Ehrmann et al., 16 J. Natl. Can. Inst. 1375-1390 (1956) and pre-equilibrated in unsupplemented Ham's F12 medium for at least 48 hr prior to use.

The culture medium used for both HUC and SV-HUC (Part B below) was Ham's F12 (GIBCO, Grand Island, N.Y.) supplemented with 1% fetal bovine serum (FBS; Hyclone, Logan UT), insulin (250 munits/ml; GIBCO), hydrocortisone (1 $\mu$g/ml; Merck, Sharpe and Dohme, West Point, Pa.), transferrin (5 $\mu$g/ml; Sigma Chemical Co., St. Louis, Mo.), a mixture of nonessential amino acids (each amino acid at 0.1 mM; Microbiological Associates, Walkersville, Md.), L-glutamine (2.0 mM; GIBCO), and dextrose (15 mM; Amend Drug and Chemical Co., Irvington, N.J.). This supplemented medium, referred to as 1% FBS-F12+ also contained penicillin (100 units/ml; Pfizer, Inc., New York, N.Y.) and streptomycin (100 $\mu$g/ml; Pfizer). Cultures were grown in humidified incubators at 37° C. in an atmosphere of 5% $CO_2$ and 95% air, and received media changes 3-4 times per week. Routine dispersion and passage of both HUC and SV-HUC were performed using 0.1% EDTA (Sigma Chemical Co.) in Hanks balanced salt solution (GIBCO) as described in C. Reznikoff, 19 In Vitro 326-343 (1983); W. Schmidt, 132 J. Urol. 1262-1264 (1984).

Cultures of SV-HUC through approximately P20 (passage twenty) were split at a ratio of 1:3 when they became confluent. SV-HUC after approximately 20 passages in culture were split at a ratio of 1:10.

B. Immortalized Cell Line—SV-HUC

For SV40 infection, primary 7 to 10 day old growing cultures of HUC were dispersed and reseeded at $1 \times 10^6$ cells/collagen-gel-coated 100 mm dish in 3 ml of serum-free F12+ which contained wild type SV40 at a multiplicity of 220 plaque-forming units/cell. After a 4 hr incubation period, at which time the cells had attached to the substrate, the virus-containing medium was replaced with 1% FBS-F12+. The SV40-infected and mock-infected control cultures were maintained in the log phase of growth by subculturing prior to confluence. At P4, control and SV40-infected cultures containing senescing cells were cocultured with preirradiated (6000 rads, cesium source) Swiss 3T3 fibroblasts as feeder cells. SV-HUC were selected by their ability to survive senescence which inevitably occurred in mockinfected HUC between P4 and P6, after 1 to 2 months in culture.

As described below, one such a cell line, SV-HUC-1, which had been in continuous culture for 30 months (70 passages, P70), has remained non-tumorigenic as assayed by over fifty subcutaneous inoculations (P15 through P70) into immature (4-6 week old) athymic nude mice. The SV-HUC-1 line also tests negative for the production of infectious SV40 virus, and positively for the presence of SV40 T antigen, showing that the cell is SV40 transformed. It also produces human keratin.

Primary cultures of HUC initiated from tissue explants grow exponentially for 3 to 4 passages, approximately 35 population doublings. Beyond this point, the proliferative capacity of the culture declines as the cells senesce. Growth of HUC routinely occurs as a continuous sheet of closely adherent cells. Between P1 and P3, SV40 infected and mock infected control cultures were morphologically indistinguishable. As cell death in both cultures progressed, the SV40-infected culture contained several small areas of rounded cells, suggestive of an increased viability. These areas were not observed in the HUC control cultures.

Since growth of HUC at clonal density is increased by coculturing HUC with feeder cells, the control and SV40 infected cultures containing the focal areas of mitotically active cells were passaged with lethally irradiated feeder cells. While all cells in the control cultures eventually senesced, the cultures of SV40 infected cells treated in the same manner contained some cells which continued to divide. When the SV40 infected cultures approached confluent density, they were serially passaged without feeder cells and continued to divide. Although SV40-transformed HUC (SV-HUC) was successfully isolated from some culture dishes which were not initially passaged with feeder cells, the SV40 infected cultures which were passaged with feeder cells yielded an increased number of transformants.

The next 5 to 10 passages of SV-HUC (P5-15) were characterized by a heterogeneous morphological appearance. As SV-HUC cultures were serially passaged, the degree of cell shedding into the medium and the numbers of giant cells gradually decreased. In contrast to cultures at earlier passages (P5-15) in which cells grew in patches with many open areas, SV-HUC cultures by P20 were capable of growing in confluent sheets, with continued propagation cultures of SV-HUC became more morphologically uniform. However, there was always a proportion of cells with a heterogeneous appearance.

The establishment of post-senescent SV-HUC cultures followed a similar progression to and apparently immortal line. SV-HUC-1 (P26) is deposited with the American Type Culture Collection, Rockville, Md. with #CRL 9520. This deposit and the other ATCC deposit described below will be made available as required by patent law. Such availability is not to be construed as a license.

C. Immunofluorescent Staining For SV40 T-Antigen And Keratin

To test for SV40 T-antigen and keratin, cells grown from SV-HUC-1 on cover glasses were washed with PBS (10 mM phosphate buffer, 133 mM NaCl, pH 7.2) and fixed with ice-cold acetone. Hamster anti-serum prepared against SV40 T-antigen (National Cancer Institute, Bethesda, Md.), fluorescein isothiocyanate (FITC-conjugated anti-hamster IgG (National Cancer Institute), rabbit anti-serum to 56 kD and 64 kD human epidermal cytokeratins (DAKO, Santa Barbara, Calif.) and FITC-conjugated anti-rabbit IgG (Jackson Labs, Avondale, Pa.) were each diluted with PBS containing 1% FBS. Non-immune rabbit serum (Jackson Labs) was used as a negative control. The fixed cells were incubated with the primary antibody for 1 hr at 37° C. in a humidified chamber, washed with PBS and subsequently incubated under the same conditions with the FITC-conjugated antibody. Following a PBS and water rinse, the cover glasses were mounted with glycerol and examined with a Nikon inverted microscope using UV epifluorescence. SV-HUC-1 stained positive for both SV40 T-antigen and cytoplasmic keratin.

D. Assay For Infectious SV40

The presence of infectious SV40 was determined as described in C. Reznikoff et al., 141 Proc. Soc. Exp. Biol. Med 740-746 (1972). Confluent cultures of African Green Monkey Kidney cells (SV40-permissive) were inoculated with media conditioned SV-HUC for 48 hr or with cell-free extracts of SV-HUC (prepared be repeated freeze thaw cycles followed by centrifugation to remove the cell debris). After a culture period of 14 days, the dishes were examined for the presence of SV40 cytopathic effect and cell lysis. Medium containing SV40 served as a positive control. SV-HUC-1 was negative for infectious SV40.

E. Tumorigenicity

Between 3 and $5 \times 10^6$ SV-HUC-1 cells were injected s.c. (0.2 ml/site) into 4-8 wk old female athymic nude mice (Harlan-Sprague-Dawley, Madison, Wis.) which were housed in a temperature (85° C.) and humidity (70%) controlled room. As a positive control, cells of the T24 bladder carcinoma cell line which give rise to tumors within 3 to 4 wk were periodically inoculated in the nude mice. Animals were examined weekly for the presence of tumors for a period of 6 months. No tumors were found in SV-HUC-1 mice.

F. Analysis Of Karyotype

For the purposes of this patent, the existence of chromosome balance type is to be determined by the following procedures. Metaphase chromosome spreads are prepared from subconfluent cultures (e.g. of SV-HUC lines) that were treated with colcemid (0.1 μg/ml, e.g. GIBCO) for 6 hr, dispersed, lysed with 75 mM KCl and fixed with ice-cold methanol/acetic acid (3/1, v/v). Chromosome spreads were prepared by dropping aliquots of the cell suspension onto cold wet slides followed by air-drying. For banding, the chromosome spreads were treated with a 0.0125% trypsin solution, rinsed, and stained with Gurr's R66 Giemsa stain. Karyotypic analysis was based on the examination of the chromosomes from 20 cells. Modal numbers were based on the counts from at least 50 cells.

A karyotypic analysis of SV-HUC-1 was performed at P15. The cell line showed a bimodal chromosomal distribution, with approximately 50% of the cells near diploid (modal number 44) and 50% of the cells in the tetraploid range (modal number 88). The chromosome pattern was heterogeneous, showing various random chromosome changes in individual cells. Both the diploid and tetraploid populations showed seven consistent marker chromosomes viz. 5p+, del(6)(p11), 9q+, 11p+, 15q-, 19p+, and an Xp+. All cells examined contained at least 5 of the 7 markers. In addition, most of the cells in both the diploid and tetraploid populations had no normal no. 15 chromosomes due to translocations resulting in the 5p+ and Xp+ markers. The tetraploid population was not an exact doubling of the diploid as it consistently had a 14q/21q translocation affecting two no. 14 and two no. 21 chromosomes, while the diploid component had normal no. 14 and 21 chromosomes but a 6q/14q translocation instead.

G. Transformation Of SV-HUC-1

SV-HUC-1 cells were exposed to MCA (3-methylcholanthrene). In all experiments, MCA-treated cells formed tumors after inoculation into nude mice while control SV-HUC-1 cells were non-tumorigenic. Both SV-HUC-1 cells from a cryopreserved stock, as well as SV-HUC-1 in continuous culture formed tumors after exposure to MCA. In the first two experiments, relatively high numbers of cells ($\geq 10^6$ per group) were exposed to carcinogen for two 48-hour periods. In the third experiment, transformation was achieved using fewer initial target cells ($6 \times 10^4$) and with only one 48-hour MCA exposure period. Tumors did not form after inoculation of all MCA-treated cells. Groups treated with the lowest concentrations of MCA ($\leq 0.01$ μg/ml)) were not tumorigenic. Furthermore, MCA treated SV-HUC-1 which were inoculated two weeks after carcinogen treatment were not tumorigenic. In contrast, the same groups were tumorigenic when inoculated after an additional four weeks of culture. Thus, a period of postreatment culture was essential for tumor formation.

Using procedures analogous to those in Part I, to date the karyotypes of four independently derived tumor lines have been analyzed. All show aneuploid human karyotypes with retention of SV-HUC-1 marker chromosomes, and formation of new tumor marker chromosomes present in every cell and unique to each tumor cell line.

One tumorigenic SV-HUC-1 derivative, MC-SV-HUC T-2 (P 10) is deposited with ATCC #CRL 9519.

H. Results

It will be appreciated that the above tumor cells have great utility in that they provide a source of human epithelial related keratins. These may be used to develop antibodies for possible diagnosis or treatment of human cancers.

Moreover, the non-tumorigenic parent cell (SV-HUC-1) provides a source of keratins for control purposes in antibody development, and may also provide a possible screening host for certain carcinogenic agents. The cells preferably are capable of being tumorigenically transformed by oncogene derived from human bladder cancer.

We claim:

1. The human uroepithelial cell that is established in culture, that is of the balance chromosome type, that produces epithelial keratin, is SV40 transformed, and is not spontaneously tumorigenic in an athymic nude mouse, and which is capable of being preserved cryogenically and tumorigenically transformed, and which is a cell from the cell line of ATCC CRL 9520.

2. The human uroepithelial cell that is tumorigenic in an athymic nude mouse, SV40 transformed, and is established in culture, is capable of being preserved cryogenically, which is capable of producing uroepithelial keratin and which is a cell from the cell line of ATCC CRL 9519.

* * * * *

UNITED STATES PATENT AND TRADEMARK OFFICE
CERTIFICATE OF CORRECTION

PATENT NO.  :  4,980,290
DATED       :  December 25, 1990
INVENTOR(S) :  Catherine A. Reznikoff; Brian J. Christian It is certified that error appears in the above-identified patent and that said Letters Patent is hereby corrected as shown below:

| | |
|---|---|
| Column 2, Line 38 | "ar" should read --are-- |
| Column 4, Line 62 | "be" should read --by-- |
| Column 5, Line 53 | "rude" should read --nude-- |
| Column 6, Line 43 | "balance" should read --balanced-- |

Signed and Sealed this

Ninth Day of June, 1992

Attest:

DOUGLAS B. COMER

*Attesting Officer*   *Acting Commissioner of Patents and Trademarks*